United States Patent [19]

Pytlewski et al.

[11] Patent Number: 4,460,797

[45] Date of Patent: Jul. 17, 1984

[54] METHOD FOR DECOMPOSITION OF HALOGENATED ORGANIC COMPOUNDS

[75] Inventors: Louis L. Pytlewski; Kenneth Krevitz, both of Philadelphia, Pa.; Arthur B. Smith, Littleton, Colo.

[73] Assignee: The Franklin Institute, Philadelphia, Pa.

[21] Appl. No.: 503,773

[22] Filed: Jun. 13, 1983

Related U.S. Application Data

[60] Division of Ser. No. 240,622, Mar. 5, 1981, , which is a continuation-in-part of Ser. No. 142,865, Apr. 21, 1980, abandoned.

[51] Int. Cl.$^3$ ............................................. C07C 37/00
[52] U.S. Cl. ......................................... 568/715; 568/739; 568/770; 568/778; 568/859; 568/891; 570/203; 570/230
[58] Field of Search ............... 568/715, 739, 769, 770, 568/774, 778, 859, 891; 570/203, 230

[56] References Cited

U.S. PATENT DOCUMENTS

| | | | |
|---|---|---|---|
| 2,448,092 | 9/1944 | Gibson | 260/683.4 |
| 2,914,558 | 11/1959 | Cooper | 260/521 |
| 3,075,021 | 1/1963 | Luvisi et al. | 260/650 |
| 3,188,357 | 6/1965 | Blumbergs | 260/655 |
| 3,595,931 | 7/1971 | Hay et al. | 260/668 |
| 3,891,717 | 6/1975 | Gilbert et al. | 260/623 |
| 3,968,177 | 7/1976 | Kaufhold et al. | 260/638 |
| 4,225,731 | 9/1980 | Marhold et al. | 568/775 |
| 4,326,090 | 4/1982 | Smith et al. | 585/469 |
| 4,327,027 | 4/1982 | Howard et al. | 260/340 |
| 4,337,368 | 6/1982 | Pytlewski et al. | 568/730 |
| 4,400,552 | 8/1983 | Pyltewski et al. | 568/715 |

FOREIGN PATENT DOCUMENTS

| | | | |
|---|---|---|---|
| 1930341 | 12/1970 | Fed. Rep. of Germany | 568/730 |
| 255880 | 7/1926 | United Kingdom . | |
| 618189 | 2/1949 | United Kingdom | 570/226 |
| 1045298 | 10/1966 | United Kingdom | 568/710 |
| 1068832 | 5/1967 | United Kingdom | 568/730 |
| 1221019 | 2/1971 | United Kingdom | 568/796 |

OTHER PUBLICATIONS

Paper; Pyltewski et al., "Conversion of PCBs and Halogenated Pesticies into Non-Toxic Materials Using New-Type of Alkali Metal Reaction", Jul. 15–16, 1979.
Paper; Pyltewski et al., "Reaction of PCBs with Sodium, Oxygen, and Polyethylene Glycols", Mar. 17, 1980.
Furukawa et al., Makromol Chemistry, vol. 38, pp. 244–247, (1960).
Toke et al., Acta Chim. Acad. Sci. Hung., vol. 93(3–4), pp. 421–424.
Toke et al., Acta Chim. Acad. Sci. Hung., vol. 100(1–4), pp. 257–264, (1979).

*Primary Examiner*—Werren B. Lone
*Attorney, Agent, or Firm*—Dann, Dorfman, Herrell and Skillman

[57] ABSTRACT

A reagent comprising the product of the reaction of an alkali metal hydroxide with a polyglycol or a polyglycol monoalkyl ether and oxygen, effects complete decomposition of halogenated organic compounds, such as polychlorinated biphenyls (PCBs), when mixed therewith in the presence of oxygen.

5 Claims, No Drawings

METHOD FOR DECOMPOSITION OF
HALOGENATED ORGANIC COMPOUNDS

This is a division, of application Ser. No. 240,622 filed Mar. 5, 1981, which latter application i.g. is a continuation-in-part of application Ser. No. 142,865, filed Apr. 21, 1980, and now abandoned.

BACKGROUND OF THE INVENTION

The present invention relates to an improved method for the decomposition of hazardous halogen-containing organic compounds, such as polychlorinated biphenyls.

The potential hazard to public health and the environment posed by the indiscriminate disposal of a variety of synthetic halogen-containing organic chemicals is well known. Compounds such as polychlorinated biphenyls (PCBs), dichlorodiphenyltrichloroethane (DDT), decachlorooctahydro-1,3,4-metheno-2H-cyclobuta-[c,d]-pentalen-2-one(Kepone ®), and 2,4,5-trichlorophenoxyacetic acid, (2,4,5-T) although having demonstrated utility, have been found in recent years to be persistent environmental poisons and, therefore, require a safe and effective means of disposal.

Halogenated organic compounds present a difficult disposal problem because of the highly stable nature of the carbon-halogen bonds present therein. The bond energy of a carbon-chlorine bond, for example, is on the order of 84 kcal./mole. Thus, many halogenated organic compounds are not only resistant to biodegradation, they cannot be degraded in a practical and effective manner by any of the well-known chemical decomposition methods. In most cases, known methods such as chlorolysis, catalytic dehydrohalogenation, molten salt reactions, ozone reactions and alkali metal reduction achieve only partial dehalogenation. Moreover, these prior art methods typically involve one or more drawbacks, such as the use of expensive reagents, inert atmospheres, extensive temperature control, complex apparatus, substantial energy consumption and the like.

In our U.S. patent applications Ser. Nos. 142,865 and 185,359, filed Apr. 21, 1980 and June 11, 1980, respectively, there is disclosed and claimed a method for the decomposition of halogenated organic compounds, especially PCBs, which represents a significant advance over the aforementioned methods of the prior art. The decomposition reagent used in practicing that method is produced by reacting an alkali metal, a polyglycol or a polyglycol monoalkyl ether, and oxygen. This reagent produces virtually complete dehalogenation of a variety of halogenated organic compounds, simply by mixing it with the halogenated compound in the presence of oxygen. Additional details of the methods of preparation and use of our previously discovered decomposition reagent are set forth in the two applications identified above, the full disclosures of which are incorporated herein by reference.

Continued efforts to improve our above-described method by enhancing its efficiency and reducing the cost and potential hazards involved in its operation, while maintaining the same high degree of effectiveness, have led to the development of the present invention.

SUMMARY OF THE INVENTION

According to one aspect of this invention, we have discovered that decomposition of halogenated organic compounds may be carried out efficiently and effectively using a reagent produced by the reaction of an alkali metal hydroxide, a polyglycol or a polyglycol monoalkyl ether, and oxygen. This decomposition reagent gives results which are comparable to those obtained using our previous method employing a decomposition reagent produced from an elemental alkali metal.

Our improved decomposition method possesses the notable advantages of our previous method, in that it does not require specialized equipment or involve extreme operating conditions. Decomposition is accomplished by simply reacting the decomposition reagent with the halogentated organic compound in the presence of oxygen. This may easily be done by mixing the reactants at room temperature in an open reaction vessel. In addition, it is possible using our improved decomposition method to scavenge hazardous substances from otherwise useful materials, thereby permitting reuse of those materials, and to convert the hazardous substances to useful products.

Our improved decomposition method also has several advantages which distinguish it from our previous method. For example, the decomposition reagent may contain a substantial amount of water, which facilitates removal of halogenated organic compounds from a water-immiscible liquid containing same because the substances remaining after decomposition form two readily separable phases, namely, a non-aqueous phase comprising the water-immiscible liquid and an aqueous phase contaning the products of the decomposition reaction. This method thus makes the water-immiscible liquid, which may be a dielectric fluid, a hydraulic fluid, or other functional fluid, available for reuse substantially free of the halogenated organic compound originally present therein. In addition, no hydrogen gas is evolved during the reactions used in carrying out our improved method. Accordingly, the mixing of oxygen and hydrogen does not occur during operation of the method, thus eliminating a possible hazard.

According to another aspect of this invention, it has been discovered that the effectiveness of our previous decomposition reagent produced from elemental alkali metal is enhanced by introducing a soluble alkali metal-containing compound into the reaction mixture comprising the decomposition reagent and the halogenated organic compound. This modification of our previous decomposition method ha been shown to significantly prolong the activity of the decomposition reagent. As compared with our previous method, this improved method may be carried out at a considerable savings for equivalent amounts of halogenated organic compound decomposed.

DESCRIPTION OF THE INVENTION

Improved Decomposition Method Using Reagent Produced From Alkali Metal Hydroxide Any of the alkali metal hydroxides may be used in practicing the method embodied in this aspect of the present invention. The hydroxides of lithium, sodium, and potassium or mixtures thereof are preferred because of their ready availability and relatively low cost. Of these, sodium hydroxide is particularly preferred because it is less expensive than the others and produces a highly reactive decomposition reagent.

A second reactant required for the production of the decomposition reagent is a compound of the general formula

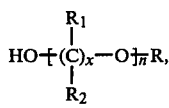

wherein R is hydrogen or lower-alkyl, $R_1$ and $R_2$ are the same or different and are selected from the group consisting of hydrogen, unsubstituted or substituted lower alkyl, unsubstituted or substituted cycloalkyl having from 5 to 8 carbon atoms, and unsubstituted or substituted aryl, n has a value from about 2 to about 400, and x has a value of at least 2, which includes polyglycols and polyglycol monoalkyl ethers. The lower alkyl radical in the foregoing formula may be methyl, ethyl, propyl, butyl, isobutyl, etc. The cycloalkyl radical may be cyclopentyl, cyclohexyl, cycloheptyl and cyclooctyl. The aryl radical may be phenyl, benzyl, biphenyl, naphthyl, etc. The substituents on the $R_1$ and $R_2$ radicals include, but are not limited to, lower-alkyl, e.g., methyl, ethyl, propyl, butyl, isobutyl, etc.; halo, e.g., chloro, bromo; nitro; sulfate; carboxyl; amino; mono- and di-lower-alkylamino, e.g. methylamino, ethylamino, dimethylamino, methylethylamino; amido; hydroxy; lower alkoxy, e.g. methoxy, ethoxy, etc.

Suitable reactants falling within the above formula include diethylene glycol, diethylene glycol monomethyl ether, polyether glycols, such as polyethylene glycols, polypropylene glycols, and polybutylene glycols and related long chain glycol monoalkyl ethers. The preferred reactants are those of the above general formula wherein $R_1$ and $R_2$ are hydrogen and x is 2. Particularly preferred are polyethylene glycols, i.e., polymers of the formula $HO-CH_2-CH_2O-_nH$, having an average molecular weight range from about 100 to about 20,000. The above-described reactants may be either liquids or solids. Those which are solids, e.g. the high molecular weight polyethylene glycols, should be melted before the reaction is begun. Neither low volatility, non-polar liquids, nor glycolic liquids in which both terminal hydroxyl groups are alkylated has been found to produce the desired decomposition.

The term "polyglycols", as used herein, is intended to signify polymers of dihydric alcohols.

Oxygen has been determined to be a necessary third reactant for the formation of the decomposition reagent. When the alkali metal hydroxide and a compound of the above general formula are reacted in the presence of oxygen, the formation of the decomposition reagent is readily observable, as the reaction mixture, which is initially clear, takes on a dark amber color. This color change does not occur in the absence of oxygen. For example, the reaction of sodium hydroxide with polyethylene glycol in a nitrogen atmosphere produces a solution that is virtually clear and ineffective as a decomposition reagent. However, when oxygen is thereafter introduced into the resultant solution, the decomposition reagent will be formed, as indicated by the aforementioned color change. Thus, the required reactants may be reacted simultaneously, or according to the two-step procedure just described.

The reaction for producing the decomposition reagent proceeds spontaneously at room temperature simply by mixing the reactants in an open reaction vessel, preferably with stirring. It is unnecessary to bubble oxygen into the reaction mixture, for atmospheric oxygen satisfies the requirements of the reaction. Thus, no temperature control or specialized equipment is required for carrying out the reaction. If desired, the reaction mixture may be heated to accelerate the rate of reaction. This reaction is considerably less exothermic than the reaction previously used to make the decomposition reagent, in which elemental alkali metal was employed as a starting material.

Theoretically, the stoichiometry of the reaction requires one mole of alkali metal hydroxide per mole of compound of the above general formula. It has determined in practice, however, that a superior decomposition reagent is produced if a slight molar excess of the alkali metal is used, i.e., on the order of 1 to 1.5 moles of alkali metal hydroxide per mole of said compound. Particularly good results are obtained when the mole ratio of alkali metal hydroxide to the compound of the above general formula is 1.1 to 1. At this particular mole ratio, the reaction is believed to produce an optimum amount of the sodium glycolate-superoxide radical complex which, as indicated in our aforementioned applications, is regarded as the moiety responsible for decomposition of halogenated organic compounds.

Solid alkali metal hydroxide or an aqueous solution thereof may be used to produce the decomposition reagent. In the latter case, the concentration of the solution may be as high as about 75 weight percent. The use of an aqueous solution of the alkali metal hydroxide has the advantage of producing a decomposition reagent having a substantial water content, which, as will be explained in more detail hereinbelow, facilitates the separation and removal of halogen-containing organic compounds from water-immiscible liquids, e.g. functional fluids, contaminated therewith. There is a limit, however, to the amount of water that may be introduced into the decomposition reagent in this manner. For example, when a 50 weight percent solution of sodium hydroxide is reacted with an approximately equimolar amount of polyethylene glycol (average M.W. of 400), the reaction mixture separates into an upper phase comprising the decomposition reagent which has a water content of about 20 weight percent and a lower aqueous phase containing unreacted sodium hydroxide. The decomposition reagent, may be readily decanted from the aqueous phase.

The extent to which water may be introduced into the decomposition regent is indeed surprising, since previous attempts at mixing water with our decomposition reagent produced from elemental alkali metals demonstrated that only about 5 weight percent of water could be added before a significant decrease in effectiveness of the decomposition reagent was observed in the treatment of functional fluids containing the halogenated organic compound. This decrease in effectiveness is believed to be due to a reduction in miscibility of the halogen containing organic compound in the decomposition reagent at a water content in excess of 5 weight percent. The relatively high water content of the decomposition reagent of the present invention has no adverse effect on its reactivity.

Once formed, the decomposition reagent may be used immediately, or it may be stored for later use. In general, the reagent may be stored for at least six months without appreciably diminishing its reactivity. Because of its caustic nature, it is recommended that the decomposition reagent be stored in a plastic container.

In order to achieve decomposition of a halogenated organic compound in accordance with this invention, all that is necessary is to add the halogenated compound to the decomposition reagent in the presence of oxygen. It has been determined that the use of pure oxygen enhances the rate of dehalogenation by a factor of five. Efforts to dechlorinate PCBs in an inert atmosphere, such as dry nitrogen, using a decomposition reagent formed from sodium hydroxide and polyethylene glycol have been unsuccessful. While decomposition will occur at room temperature, the mixture may be heated to speed the rate of reaction. Heating to a temperature in the range of about 40° C. to about 180° C. has been found to produce satisfactory results. Of course, the temperature may vary depending upon the nature of the decomposition reagent used and the halogenated organic compound being decomposed.

Representative halogenated organic compounds which may be decomposed in accordance with the present invention include hexachlorocyclohexane, hexachlorobenzene, trichlorobenzene, tetrachlorobenzene, dichlorophenol, pentachlorophenol, dichlorodiphenyltrichloroethane, decachlorooctahydro-1,3,4-metheno-2H-cyclobuta-[c,d]-pentalen-2-one and polychlorinated biphenyl. As mentioned above, this invention is particularly useful for the decomposition of the polychlorinated biphenyls (PCBs).

Our improved decomposition method is not only applicable to the decomposition of halogenated organic compounds that are uncontaminated with other substances, e.g., "neat" PBCs, but also provides a very effective and efficient way for decomposing and disposing of halogenated organic compounds that are dissolved in otherwise useful water-immiscible liquids. Reuse of such useful liquids may be accomplished very easily with our improved decomposition method and employing a reagent produced from an aqueous alkali metal hydroxide solution. This reagent is simply added to the water-immiscible liquid containing the dissolved halogenated organic compound in the presence of oxygen, and the substances remaining after the decomposition reaction is complete separate into two liquid phases. One phase comprises the water-immiscible liquid substantially free of the halogenated organic compound. The other phase is an aqueous phase containing the products from the decomposition of the halogenated organic compound, to the extent these products are water soluble. The two phases are readily separated one from the other, for example, by decantation, and the water-immiscible liquid is available for reuse. This procedure may be used to advantage for the reclamation of dielectric fluids or other functional fluids which are contaminated with PCBs. It is particularly effective as a means of reclassifying PCB Transformers or PCB-Contaminated Transformers to Non-PCB Transformers, i.e. transformers containing PCBs at a concentration of less than 50 ppm, as provided in the U.S. Environmental Protection Agency's final PCB ban rule, which became effective July 2, 1979.

The technique just described could not be employed using our previous method since water sufficient to effect the necessary phase separation could not be introduced into the decomposition reagent without substantially reducing its effectiveness, as previously noted.

The order in which the steps of the decomposition method are carried out is not considered critical. Thus, while a presently preferred order has been described hereinabove, the method may be practiced otherwise. For example, the halogen-containing organic compound may be added to the liquid reactant in the presence of oxygen prior to the addition of the alkali metal hydroxide, or the alkali metal hydroxide and the halogenated organic compound may be added simultaneously to the liquid reactant. As another alternative, the alkali metal hydroxide and halogen-containing organic compound may be added to the liquid reactant in an oxygen-free atmosphere, e.g., pure nitrogen, with subsequent introduction of oxygen into the reaction mixture to form the decomposition reagent, whereupon complete dechlorination of the halogenated compound is rapidly achieved.

Relatively speaking, the method embodied in this aspect of the invention is safer in operation than our previous method, in that it involves no serious materials handling problems and produces no potentially hazardous by-products. Since alkali metal hydroxides rather than alkali metals are employed in preparing the decomposition reagent, the standard safety precautions ordinarily observed when handling alkali metals are unnecessary. Moreover, since no hydrogen gas is evolved during preparation of the decomposition reagent, the possibility of forming a potentially explosive mixture of hydrogen and oxygen is eliminated. Consequently, an open flame may be used to heat the reaction in which the decomposition reagent is formed.

Decomposition of halogenated organic compounds using the method of the present invention produces relatively innocuous products, the principal ones being sodium chloride, and various dehalogenated organic compounds. These latter products may be converted to polyhydroxylated compounds which are useful as reactants in the production of polymers, as plasticizers, as anti-oxidants, and as solvents for high temperature reactions. The products are readily recoverable from the reaction medium by the separation technique described hereinabove. Considering that the useful compounds produced from the recovered products may be marketed, at least a portion of the operating costs of the present method should be recoupable.

This aspect of the invention will be further understood by reference to the following examples.

EXAMPLE 1

Preparation of Decomposition Reagent Reagent Using Aqueous NaOH Solution

A sodium hydroxide-polyethylene glycol decomposition reagent (referred to in these examples as NaOH-PEG) was prepared by mixing in a beaker open to the atmosphere 10 ml of a 50 weight percent aqueous sodium hydroxide solution and 40 ml. of polyethylene glycol having an average M.W. of 400 (referred to in these examples as PEG 400). The mixture was heated to 95° C. with stirring for 15 minutes. Stirring was discontinued and after a short period two distinct phases formed. The upper phase appeared dark brown and was similar in appearance to the reagent we previously prepared from sodium metal and PEG 400. The lower phase appeared clear, and its volume was about 10 ml.

An additional 30 grams of solid NaOH pellets were added to the beaker in three 10 gram portions. The temperature of the contents of the beaker had to be raised in order to dissolve all of the added NaOH, complete dissolution occurring at a temperature of 153° C. During the addition of the solid NaOH, the volume of the lower phase appeared to about double in volume.

EXAMPLE II

Preparation of Decomposition Reagent Using Solid NaOH

The NaOH-PEG reagent was prepared by mixing 10 grams of solid NaOH with 50 ml. of PEG 400 in an open beaker and heating the mixture at 120° C. for about 2 hours. The appearance of the dark brown color indicated that the reagent had been formed.

EXAMPLE III

Dechlorination of PCBS

In one test, 15 ml of the decomposition reagent prepared in Example I was added to 1 gram of Inerteen ® (neat) and heated to 145° C. with stirring. Inerteen ® is a trade name for polychlorinated biphenyl (PCB) formerly produced by Westinghouse, Inc. Samples of the reaction mixture were taken at one-half hour intervals, extracted with cyclohexane and analyzed by a Hewlett Packard No. 5700 gas chromatograph with an electron capture detector (GC/EC) operated under the following conditions: Column packing: Supelco Inc. 1.5% SP-2250/1.95% SP-2401 on 100/200 mesh Supelcoport; Injector and detector temperature: 250° C.; Column temprature: 200° C.; Carrier gas: argon containing 10 weight percent methane; Flow rate: 40 ml./min. After one hour, GC/EC indicated that complete dechlorination of the Inerteen ® had been effected.

In another test, a 2 gram sample of Inerteen ® was mixed with the decomposition reagent of Example II, and the temperature of the mixture was maintained at about 120° C. Analysis of the decomposition reaction mixture by GC/EC (operated under the same conditions described above) indicated that the chlorine content of the PCBS had been reduced by about approximately 85 to 90%.

EXAMPLE IV

Decomposition of 1,2-Dichlorophenol 10 grams of the NaOH-PEG reagent of Example I and 1 gram of 1,2-dichlorophenol were mixed and heated at 90° C. for 1 hour in a beaker which was open to the atmosphere. Analysis of the decomposition reaction mixture by GC/EC (operated under the same conditions described in Example III) showed approximately 85 to 90% dechlorination of the 1,2-dichlorophenol.

Improved Decomposition Method Using Reagent Derived From Elemental Alkali Metal and Supplemented With Alkali Metal Hydroxide This aspect of the invention relates to the enhancement of the reactivity of the decomposition reagent prepared by the reaction of an alkali metal and a compound of the general formula set forth hereinabove in the presence of oxygen. Such decomposition reagents are the subject of our two earlier patent applications referred to previously.

We have now discovered that the reactivity of our previous decomposition reagents is enhanced by introducing into the reaction mixture comprising the decomposition reagent and the halogenated organic compound an alkali metal containing-compound which is soluble therein.

Although the scientific principle responsible for the enhanced reactivity of the decomposition reagent is not clearly understood, it is believed that the added alkali metal-containing compound, in effect, impedes degradation of the moiety which causes decomposition of the halogenated organic compounds. This moiety is thought to be a complex formed between an alkali metal and a compound of the above general formula, e.g., sodium and polyethylene glycol, which has a superoxide radical associated therewith, and which is believed to exert something of a catalytic effect on the decomposition reaction. It is theorized that the complex undergoes degradation in the formation of the alkali metal salt which is one of the principal decomposition reaction products. The presence of the added alkali metal-containing compound in the decomposition reaction mixture is believed to enhance the stability of the complex by introducing an additional source of alkali metal ions which are available to keep the complex intact or to contribute to the formation of the alkali metal chloride product. In this way, the reactivity of the complex is prolonged.

The alkali metal-containing compound may be introduced into the decomposition reaction mixture in solid form, or an aqueous solution of the alkali metal hydroxide may be used. Particularly good results have been obtained by adding solid sodium hydroxide to a decomposition reagent produced from sodium and polyethylene glycol. For example, the addition of sodium hydroxide, in an amount which is the molar equivalent of the sodium in the decomposition reagent has been found to improve the reactivity of this particular decomposition reagent approximately twofold.

In this aspect of the invention also, the introduction of water into the decomposition reaction mixture facilitates the reclamation of useful water-immiscible liquids in which halogenated organic compounds are dissolved.

Although the various aspects of the present invention have been exemplified with reference to the decomposition of specific halogenated organic compounds, these methods may be used with success for the decomposition of a wide variety of other halogen-containing organic compounds. Mixtures of organic halogenated compounds other than PCBs may also be decomposed by these methods.

Those skilled in the art will appreciate that the methods disclosed in the foregoing examples are merely illustrative and are capable of wide variation and modification without departing from the scope of the invention as defined in the appended claims.

We claim:

1. The product of the reaction of an alkali metal hydroxide, a reactant having the general formula

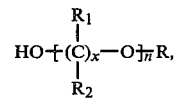

wherein R is hydrogen or lower alkyl, $R_1$ and $R_2$ are the same or different and are selected from the group consisting of hydrogen, unsubstituted or substituted lower alkyl, unsubstituted or substituted cycloalkyl having from 5 to 8 carbon atoms, and unsubstituted or substituted aryl, n has a value from about 2 to about 400 and x has a value of at least 2, and oxygen.

2. The product claimed in claim 1 wherein the alkali metal hydroxide is selected from the group consisting of sodium hydroxide, lithium hydroxide potassium hydroxide mixtures thereof and $R_1$ and $R_2$ in the general formula are hydrogen and x is 2.

3. The product of the reaction claimed in claim 1 wherein the alkali metal hydroxide is sodium hydroxide and the reactant is polyethylene glycol.

4. The product claimed in claim 1 wherein the alkali metal hydroxide is in the form of an aqueous solution.

5. A method for the preparation of a decomposition reagent for halogenated organic compounds, comprising:

a. reacting an alkali metal hydroxide a reactant having the general formula

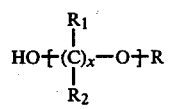

wherein R is hydrogen or lower alkyl, $R_1$ and $R_2$ are the same or different and are selected from the group consisting of hydrogen, unsubstituted or substituted lower alkyl, unsubstituted or substituted cycloalkyl, having from 5 to 8 carbon atoms and unsubstituted or substituted aryl, n has a value of from 2 to about 400, and x has a value of at least 2, and oxygen to form said decomposition reagent.

* * * * *

UNITED STATES PATENT AND TRADEMARK OFFICE
CERTIFICATE OF CORRECTION

PATENT NO. : 4,460,797

DATED : July 17, 1984

INVENTOR(S) : Louis L. Pytlewski et al.

It is certified that error appears in the above-identified patent and that said Letters Patent is hereby corrected as shown below:

Cancel claims 1 through 4.

Claim 5 should read:

19. A method for the preparation of a decomposition reagent for halogenated organic compounds comprising:

reacting (a) an alkali metal hydroxide, (b) a reactant having the general formula:

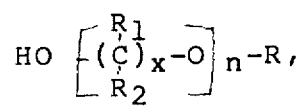

UNITED STATES PATENT AND TRADEMARK OFFICE
CERTIFICATE OF CORRECTION

PATENT NO. : 4,460,797
DATED : July 17, 1984
INVENTOR(S) : Louis L. Pytlewski et al.

It is certified that error appears in the above-identified patent and that said Letters Patent is hereby corrected as shown below:

wherein R is hydrogen or lower alkyl, $R_1$ and $R_2$ are the same or different and are selected from the group consisting of hydrogen, unsubstituted or substituted lower alkyl, unsubstituted or substituted cycloalkyl, having from 5 to 8 carbon atoms and unsubstituted or substituted aryl, n has a value of from about 2 to about 400, and x has a value of at least 2, and (c) oxygen, the molar ratio of alkali metal hydroxide to said reactant being 1:1, or greater, said reaction being

UNITED STATES PATENT AND TRADEMARK OFFICE
CERTIFICATE OF CORRECTION

PATENT NO. : 4,460,797

DATED : July 17, 1984

INVENTOR(S) : Louis L. Pytlewski et al.

It is certified that error appears in the above-identified patent and that said Letters Patent is hereby corrected as shown below:

carried out in the absence of a catalyst.

On the title page, "5 Claims" should read -- 1 Claim --.

Signed and Sealed this

Twelfth Day of February 1985

[SEAL]

Attest:

DONALD J. QUIGG

Attesting Officer  Acting Commissioner of Patents and Trademarks